United States Patent [19]

Calabretta

[11] Patent Number: 5,362,631
[45] Date of Patent: Nov. 8, 1994

[54] C-MYB TRANSFECTED T98G CELLS WHICH PRODUCE GM-CSF AND STEM CELL FACTOR

[75] Inventor: Bruno Calabretta, Philadelphia, Pa.

[73] Assignee: Thomas Jefferson University, Philadelphia, Pa.

[21] Appl. No.: 99,868

[22] Filed: Jul. 29, 1993

[51] Int. Cl.$^5$ .................. C12N 5/22; C12N 15/19
[52] U.S. Cl. .................. 435/69.5; 435/69.4; 435/240.2
[58] Field of Search ............ 435/69.4, 69.5, 240.2

[56] References Cited

PUBLICATIONS

Reiss, K., et al. (1991) Cancer Res. 51:5997–6000.
Gonda, T. J., et al. (1989) EMBO J. 8:1767–75.
Nohava, K., et al. (1992) Eur. J. Immunol. 22:2539–45.
McMahon, J., et al. (1988) Oncogere 3:717–20.
Yanagisawa, H., et al. (1991) Biochim. Biophys. Acta 1088:380–84.
Collins, S. J., Gallo, R. C., and Gallagher, R. E., (1977) Continuous Growth and Differentiation of Human Myeloid Leukemic Cells in Suspension Culture, Nature, 270:347.
Pagoraro, L., Matera L., Ritz, A., Levis, A., Palumbo, A., Biagini, G., (1983) Establishment of a Ph$^1$ Positive Human Cell Line (BV173), J. Natl. Cancer Inst., 70:447.
Majello, B., Kenyon, L. C. and Dalla–Favera, R. (1986) Huan c-myb Proto-oncogene: Nucleotide Sequence of cDNA and Organization of Genomic Locus, Proc. Natl. Acad. Sci., USA, 83:9616.
Tukunaga, K. et al., (1986), Nucleotide Sequence for a Full–Length cDNA for Mouse Cytoskeletal $\beta$–actin mRNA, Nucl. Acid. Res. 14:2829.

Primary Examiner—Robert J. Hill, Jr.
Assistant Examiner—David L. Fitzgerald
Attorney, Agent, or Firm—Jane Massey Licata

[57] ABSTRACT

A c-myb transfected cell line capable of producing a selected growth factor is provided. In a preferred embodiment, human glioblastoma cells are co-transfected with a first plasmid containing human c-myb DNA and second plasmid containing the gene encoding hygromycin resistance. Methods of producing selected growth factors employing cell line are also provided.

9 Claims, 8 Drawing Sheets

C-MYB
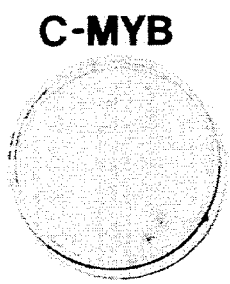 C 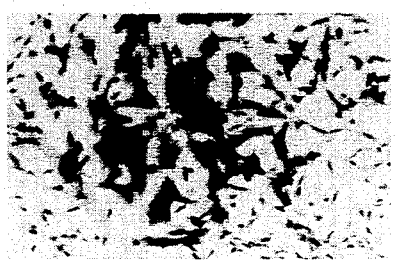 FIG.2A
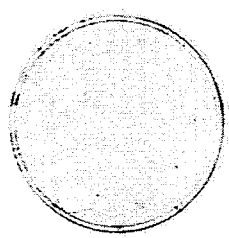 S 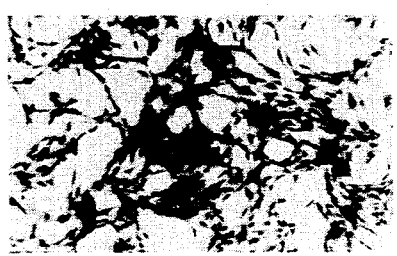 FIG.2B
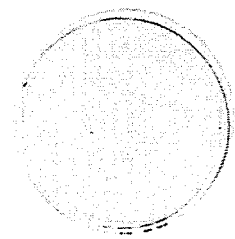 AS 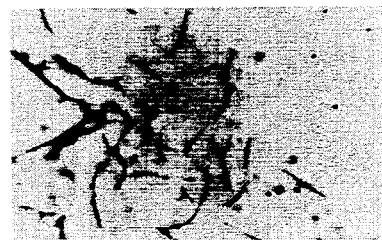 FIG.2C

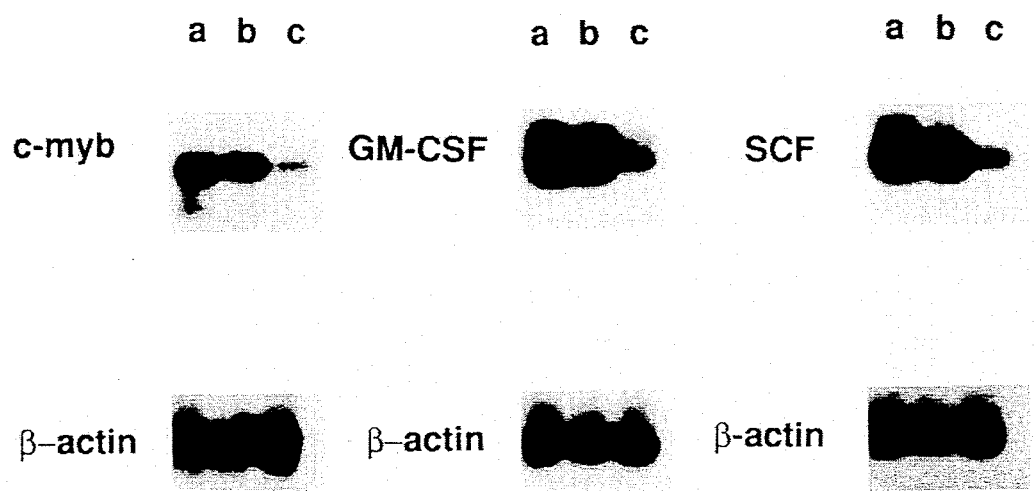

FIG.4A
c-myb 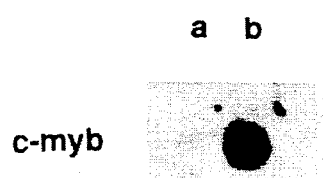
β-actin 
FIG.4B
GM-CSF 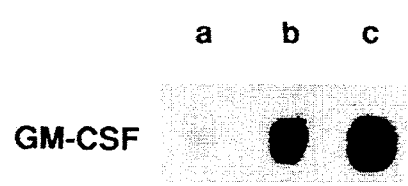
β-actin 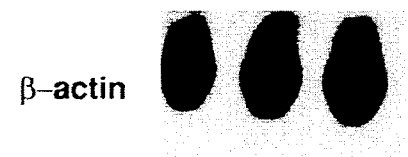
FIG.4C
SCF 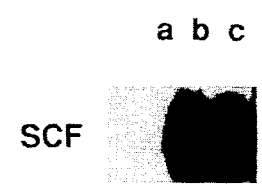
β-actin 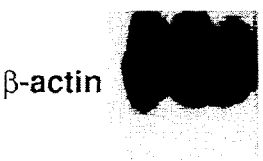

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

GCCCGAACAC CCCGGCAC        18

( 2 ) INFORMATION FOR SEQ ID NO: 2:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 2:

GTGCCGGGGT CTTGGGGC        18

( 2 ) INFORMATION FOR SEQ ID NO: 3:

( i ) SEQUENCE CHARACTERISTICS:
        ( A ) LENGTH: 23
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 3:

ATTAGGTAAT GAATTGTAGC CAG        23

( 2 ) INFORMATION FOR SEQ ID NO: 4:

( i ) SEQUENCE CHARACTERISTICS:
　　　　　　　　( A ) LENGTH: 23
　　　　　　　　( B ) TYPE: Nucleic Acid
　　　　　　　　( C ) STRANDEDNESS: Single
　　　　　　　　( D ) TOPOLOGY: Linear ( i v ) ANTI-SENSE: No ( x i ) SEQUENCE DESCRIPTION: SEQ ID NO: 4:

ACTTAGAGTA ATGCTTTTAC TGA          23

( 2 ) INFORMATION FOR SEQ ID NO: 5:

( i ) SEQUENCE CHARACTERISTICS:
　　　　　　　　( A ) LENGTH: 51
　　　　　　　　( B ) TYPE: Nucleic Acid
　　　　　　　　( C ) STRANDEDNESS: Single
　　　　　　　　( D ) TOPOLOGY: Linear ( i v ) ANTI-SENSE: No ( x i ) SEQUENCE DESCRIPTION: SEQ ID NO: 5:

ATTTTTTTAA AAAAAAACAT AAAATGATTT ATCTGGTATT TTAAAGGATC C          51

( 2 ) INFORMATION FOR SEQ ID NO: 6:

( i ) SEQUENCE CHARACTERISTICS:
　　　　　　　　( A ) LENGTH: 20
　　　　　　　　( B ) TYPE: Nucleic Acid
　　　　　　　　( C ) STRANDEDNESS: Single
　　　　　　　　( D ) TOPOLOGY: Linear ( i v ) ANTI-SENSE: No ( x i ) SEQUENCE DESCRIPTION: SEQ ID NO: 6:

ATGTGAATGC CATCCAGGAG          20

( 2 ) INFORMATION FOR SEQ ID NO: 7:

( i ) SEQUENCE CHARACTERISTICS:
　　　　　　　　( A ) LENGTH: 20
　　　　　　　　( B ) TYPE: Nucleic Acid
　　　　　　　　( C ) STRANDEDNESS: Single
　　　　　　　　( D ) TOPOLOGY: Linear ( i v ) ANTI-SENSE: No ( x i ) SEQUENCE DESCRIPTION: SEQ ID NO: 7:

CTTGTAGTGG CTGGCCATCA          20

( 2 ) INFORMATION FOR SEQ ID NO: 8:

( i ) SEQUENCE CHARACTERISTICS:
　　　　　　　　( A ) LENGTH: 20
　　　　　　　　( B ) TYPE: Nucleic Acid
　　　　　　　　( C ) STRANDEDNESS: Single
　　　　　　　　( D ) TOPOLOGY: Linear ( i v ) ANTI-SENSE: No ( x i ) SEQUENCE DESCRIPTION: SEQ ID NO: 8:

TAGAGACACT GCTGCTGAGA          20

( 2 ) INFORMATION FOR SEQ ID NO: 9:

( i ) SEQUENCE CHARACTERISTICS:
　　　　　　　　( A ) LENGTH: 21
　　　　　　　　( B ) TYPE: Nucleic Acid
　　　　　　　　( C ) STRANDEDNESS: Single -continued ( D ) TOPOLOGY: Linear ( i v ) ANTI-SENSE: No ( x i ) SEQUENCE DESCRIPTION: SEQ ID NO: 9:

ATGAAGAAGA CACAAACTTG G                                              21

( 2 ) INFORMATION FOR SEQ ID NO: 10:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 10:

GCTCAGAAGA TCAGTCAAGC T                                              21

( 2 ) INFORMATION FOR SEQ ID NO: 11:

( i ) SEQUENCE CHARACTERISTICS:
        ( A ) LENGTH: 39
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 11:

GCCGAGCTGG ACAGCACCGT GCTCCTGACC CGCTCTCTC                            39

( 2 ) INFORMATION FOR SEQ ID NO: 12:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 12:

AAGATTCATA CCTCAGAGCG                                                20

( 2 ) INFORMATION FOR SEQ ID NO: 13:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 13:

ATGAGATCAC CTAGTCCACC                                                20

( 2 ) INFORMATION FOR SEQ ID NO: 14:

( i ) SEQUENCE CHARACTERISTICS:
        ( A ) LENGTH: 30
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 14:

AGCCCAGACT CGAATTCTGG TTCTGCCAAA                                      30

( 2 ) INFORMATION FOR SEQ ID NO: 15:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 15:

ATGAACTGTG TTTGCCGC                                                   18

( 2 ) INFORMATION FOR SEQ ID NO: 16:

( i ) SEQUENCE CHARACTERISTICS:
        ( A ) LENGTH: 18
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 16:

CCCCTGAGCT GGGAATTT                                                  18

( 2 ) INFORMATION FOR SEQ ID NO: 17:

( i ) SEQUENCE CHARACTERISTICS:
        ( A ) LENGTH: 39
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 17:

GCCGAGCTGG ACAGCACCGT GCTCCTGACC CGCTCTCTC             39

( 2 ) INFORMATION FOR SEQ ID NO: 18:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 18:

AAGCTTGCTG AGAGTGGCTG C                                            21

( 2 ) INFORMATION FOR SEQ ID NO: 19:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 19:

CAGAGAACTT TAGCCTTTCT C                                            21

C-MYB TRANSFECTED T98G CELLS WHICH PRODUCE GM-CSF AND STEM CELL FACTOR

This invention was made in the course of research funded by the National Institute of Health under grant number CA09670. This U.S. government may have certain rights in this invention.

BACKGROUND OF THE INVENTION

Hematopoietic tissue is constantly renewed through the proliferation and differentiation of stem cells residing in the bone marrow in close contact with multiple adherent (stromal) cells that comprise the hematopoietic microenvironment (HM). In vitro stromal cells form fibroblast colonies (CFU-F) which, under defined conditions support long-term bone marrow growth of primitive hematopoietic stem cells (LTBMC-long term bone marrow cultures, or Dexter-type cultures). The interactions between the hematopoietic cells and the microenvironment are not well understood, due to the cellular heterogeneity of this microenvironment and to the difficulties in isolating homogeneous populations of its components for genetic and functional studies. The development of the PCR technology has enabled detection of growth factor transcripts in stromal marrow fibroblasts, suggesting that, via these cytokines, these cells play an important role in hematopoiesis in mammals in vivo.

Different experimental approaches have revealed that the protooncogene c-myb plays an important role in regulating not only hematopoietic cell growth, but also proliferation of non-hematopoietic cells. Treatment with synthetic c-myb antisense oligodeoxynucleotides inhibits formation of colonies derived from normal hematopoietic progenitors. Inactivation of the endogenous c-myb gene by homologous recombination in mouse embryonic stem cells drastically impairs liver hematopoiesis. There remains a need to determine the role and effect of c-myb regulation on other cell functions.

SUMMARY OF THE INVENTION

The c-myb protooncogene plays a major role in regulating the process of in vitro and in vivo hematopoiesis via its activity as transcriptional regulator in hematopoietic progenitor cells. Since the bone marrow microenvironment appears to regulate in vivo hematopoiesis by maintaining the growth of multipotent progenitors via secretion of specific cytokines, whether c-myb is also required for the proliferation of and/or cytokine production by stromal cells that generate fibroblast-like colonies (CFU-F) was investigated. Using the reverse transcriptase-polymerase chain reaction (RT-PCR) technique, low levels of c-myb mRNA transcripts in human normal bone marrow fibroblasts were detected. Treatment of these cells with c-myb antisense oligodeoxynucleotides caused down-regulation of c-myb expression, decrease in the number of marrow CFU-F colonies (~54% inhibition), and in the cell number within residual colonies (~80%), and down-regulation of granulocyte/macrophage-colony stimulation factor (GM-CSF) and stem cell factor (SCF) mRNA expression. Transfection of T98G glioblastoma cells, in which expression of c-myb, GM-CSF and SCF mRNAs is undetectable or barely detectable, with a plasmid containing a full-length c-myb cDNA under the control of the SV40 promoter induced the expression of biologically active SCF and GM-CSF in these cells. Regulation of GM-CSF expression by c-myb was due in part to transactivation of the GM-CSF promoter. These results indicate that, in addition to regulating hematopoietic cell proliferation, c-myb is also required for proliferation of and cytokines synthesis by bone marrow fibroblasts.

In accordance, a primary object of the present invention is to provide a c-myb transfected cell line capable of producing a selected growth factor.

Another object of the present invention is to provide a method of producing a selected growth factor which comprises culturing selected cells, co-transfecting the cultured cells with a plasmid containing human c-myb cDNA and a plasmid containing the gene encoding hygromycin resistance, selecting cultured cells containing hygromycin B, culturing these cells in medium containing hygromycin B, and recovering selected growth factor from the medium.

BRIEF DESCRIPTION OF THE DRAWINGS

FIGS. 2A, 2B and 2C show the effect of c-myb antisense oligodeoxynucleotides on human CFU-F NBM colony formation. The left panel of each figure shows the effect of c-myb oligomers on the number of CFU-F colonies from NBM cells. The corresponding higher magnification pictures (right panels) show the effect of c-myb oligomers on CFU-F colonies cellularity. FIG. 2A shows untreated cultures; FIG. 2B, c-myb sense-treated cultures; and FIG. 2C c-myb antisense-treated cultures.

FIGS. 3A, 3B and 3C show the effect of c-myb antisense oligodeoxynucleotides on c-myb, GM-CSF and SCF mRNA levels respectively, in human marrow stromal fibroblasts. Lane a of each figure is untreated cells; lane b is c-myb-sense-treated cells, and lane c is c-myb antisense-treated cells. As control, $\beta$-actin mRNA expression was evaluated in each sample. Identical qualitative results were obtained with 30 or 40 RT-PCR amplification cycles.

FIG. 4A, 4B and 4C show expression of c-myb, GM-CSF and SCF in T98G and SV-myb T98G cells. RNA extracted from T98G glioblastoma cells (shown in lane a of each figure), SV-myb T98G cells (shown in lane b), PHA-stimulated PBMC (shown in FIG. 4B as lane c) and HTB cells (shown in FIG. 4C as lane a) was analyzed by RT-PCR for c-myb (FIG. 4A), GM-CSF (FIG. 4B), and SCF (FIG. 4C) expression. As a control $\beta$-actin mRNA expression was analyzed in all samples.

DETAILED DESCRIPTION OF THE INVENTION

Figure 1:
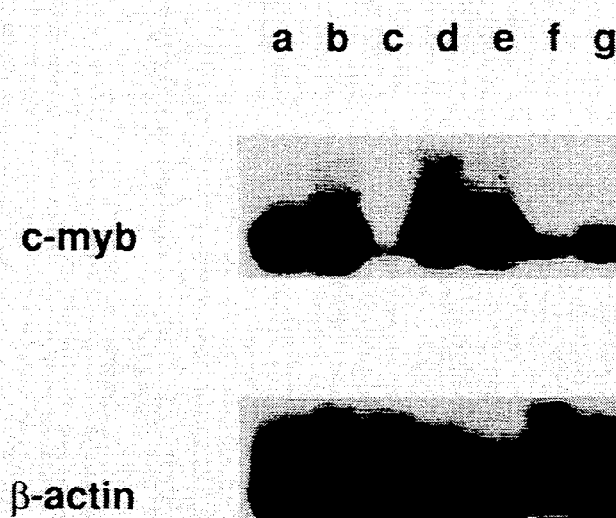
FIG. 1 shows c-myb mRNA levels in human hematopoietic and non-hematopoietic cells. Total RNA extracted from $5 \times 10^4$ HL-60 (shown in lane a), BV-173 (shown in lane b), T98G (shown in lane c), SV-myb T98G (shown in lane d), marrow mononuclear cells enriched in CD34+ cells (shown in lane e), WI-38 (shown in lane f), and human marrow stromal fibroblasts (shown in lane g), was analyzed by RT-PCR technique for c-myb and $\beta$-actin expression.

It has been shown that the product of c-myb plays an important role in normal and leukemic hematopoiesis, perhaps by directly regulating the proliferation of normal early hematopoietic progenitors and leukemic cells. The role of c-myb does not appear to be restricted to hematopoietic cells, since other normal and neoplastic non-hematopoietic cells expressing c-myb require this gene for proliferation.

Because normal bone marrow contains non-hematopoietic adherent progenitor cells (CFU-F) capable of forming fibroblast colonies that support long-term growth of hemopoietic cells in vitro, whether c-myb is expressed in these cells and whether it is important for their proliferation and function was investigated. Downregulation of c-myb expression in marrow stromal cells was associated with inhibition of colony formation derived from CFU-F progenitors (~54%, inhibition of colony formation) and with a reduced number of cells in each residual colony (~80% reduction), indicating that the relatively low levels of c-myb expression in these cells were nevertheless important for their proliferation. Marrow fibroblasts appear to express c-myb mRNA at levels lower than those of normal or leukemic hematopoietic cells but significantly higher than those found in the WI-38 human fibroblasts, cells considered to be negative for c-myb expression. The limited effect of c-myb antisense oligodeoxynucleotide on marrow fibroblast proliferation may reflect the requirement by these cells of the function of other members of the myb gene family, such B-myb which we have recently shown to behave as a c-myb functional equivalent in fibroblasts. Nevertheless, the data shown here indicate that the role of c-myb is more general than previously thought and are consistent with similar findings in other non-hematopoietic systems such as that of colon carcinoma and neuroblastoma cell proliferation and normal smooth muscle cell proliferation.

To further evaluate the role of c-myb expression for stromal fibroblast cell function, whether cytokine production was regulated by c-myb was assessed. Several lines of evidence support this hypotheses: 1) downregulation of c-myb expression in stromal fibroblasts was associated with specific decrease in GM-CSF and SCF mRNA levels; 2) constitutive expression of c-myb in a glioblastoma cell line with low or undetectable levels of endogenous c-myb was associated with upregulation of GM-CSF and SCF mRNAs and proteins; 3) c-myb transactivated the expression of a reporter gene driven by a segment of the 5' flanking region of the human GM-CSF gene. Although it cannot be excluded that downregulation of GM-CSF and SCF expression in marrow fibroblasts exposed to c-myb antisense oligodeoxynucleotides is, at least in part, a consequence of the growth inhibition of these cells, the observation that GM-CSF and SCF expression is upregulated in T98G cells whose growth is independent of c-myb expression, and that c-myb has a direct effect on the GM-CSF promoter makes it unlikely that GM-CSF and SCF production are solely related to proliferative effects. The significance of the functional link between c-myb and hematopoietic growth factors may not be restricted to marrow fibroblasts; a subset of primary leukemic cells expresses GM-CSF. The overexpression of c-myb often observed in leukemic cells leads to autocrine cytokine expression which, in turn, contributes to the growth advantage of leukemic cells.

2B and 2C illustrate these effects in a representative experiment.

TABLE 1

Inhibition of CFU-F Colony Formation by c-myb Sense or Antisense 18-mer Oligodeoxynucleotides

|  | Experiment | | | |
| --- | --- | --- | --- | --- |
|  | 1 | 2 | 3 | 4 |
| Control Colony | 14.4 ± 2° | 34.5 ± 3.5 | 16.7 ± 2.3 | 26.8 ± 6.8 |
| No. Cells/Colony | 1718.5 ± 127.3 | 500 ± 50.9 | 1781 ± 88.1 | 110.3 ± 41.7 |
| Sense Colony No. | 17.5 ± 0.7 | 47.08 ± 2.8 | 13.5 ± 0.7 | 31 ± 4.2 |
| Cells/Colony | 1843 ± 391.2 | 578.5 ± 44.5 | 1408.3 ± 218.2 | 65 ± 19.3 |
| Antisense Colony | 7.5 ± 2.1 | 17.7 ± 1.5 | 7.01 ± 1.4 | 16.25 ± 3.4 |
| No. Cells/Colony | 327.3 ± 40.2 | 90.3 ± 32 | 309.2 ± 47.3 | 20.2 ± 5.9 |
| % Inhibition Colony Growth* | 57.2 | 62.4 | 48.7 | 47.5 |
| (Significance) | $P < 0.001$ | $p < 0.002$ | $p < 0.005$ | $p < 0.03$ |
| % Inhibition Cells/Colony** | 82.2 | 84.3 | 78.8 | 68.9 |
| (Significance) | $p < 0.001$ | $p < 0.005$ | $p < 0.005$ | $p < 0.015$ |

°Numbers are mean ± SD from quadruplicate plates.
*Calculated from the ratio between colony number in sense- and antisense-treated cultures.
**Calculated from the ratio of number of cells/colony (10 for each group) in sense- and antisense-treated cultures.

In summary, c-myb appears to play a role in regulating both proliferation and cytokine production in marrow fibroblasts. Although the mechanisms involved in this function remain unknown, the data show the importance of the role of c-myb activation in hematological malignancies.

Detection of c-mRNA in Bone Marrow Stromal Fibroblasts

C-myb mRNA levels are relatively abundant in undifferentiated and proliferating hematopoietic cells, but are undetectable or present in few copies in other normal cell types. To determine whether c-myb mRNA is present in marrow stromal fibroblasts and to compare its expression to that found in hematopoietic cells, RNA was extracted from an equal number of cells from different sources and mRNA levels were measured by RT-PCR analysis (FIG. 1). High levels of c-myb mRNA were detected in the myeloid leukemia cell line HL 60 (Collins, S. J., Gallo, R. C., and Gallagher, R. E., (1977) Continuous Growth and Differentiation of Human Myeloid Leukemic Cells in Suspension Culture, Nature, 270:347), (lane a); in the Philadelphia lymphoid leukemia line BV173 (Pagoraro, L., Matera L., Ritz, A., Levis, A., Palumbo, A., Biagini, G., (1983) Establishment of a Ph[1] Positive Human Cell Line (BV173), J. Natl. Cancer Inst., 70:447) (lane b); in normal marrow mononuclear cells enriched in early progenitors (CD34+ cells) (lane e); and in the glioblastoma T98G line transfected with a human c-myb cDNA plasmid (SV-myb T98G) (lane d). C-myb mRNA levels were barely detectable in WI38 human fibroblasts (lane f), and in the parental T98G cells (lane c). Intermediate c-myb mRNA levels were detected in marrow stromal fibroblasts (lane g).

Effect of c-myb Oligomers on CFU-F Colony Growth

To determine whether cloning efficiency of stromal fibroblasts derived from human normal bone marrow depends on c-myb expression, the effect of c-myb sense or antisense oligodeoxynucleotides (80 µg/ml at time 0; 40 µg/ml after 24 hours), on stromal fibroblast colony formation was analyzed in 14-day cultures. In four separate experiments, untreated and sense-treated cells formed a similar number of colonies, each containing a similar number of cells. In contrast, cultures treated with c-myb antisense oligodeoxynucleotides showed a ~54% decrease in colony number and an ~80% decrease in cell content per colony (Table 1). FIGS. 2A, 2B and 2C illustrate these effects in a representative experiment.

Effect of c-myb Antisense Oligonucleotides on c-myb, GM-CSF and SCF mRNA Levels in Stromal Cells To determine whether the inhibition of stromal fibroblasts colony formation was associated with down-regulation of c-myb expression, c-myb mRNA levels were determined by RT-PCR after exposure of stromal cells collected after the 4th passage, to c-myb sense or antisense oligodeoxynucleotides. These cells showed an intense staining for type I collagen, and were negative for the expression of factor VIII, CD14 and CDw32 normally expressed by endothelial cells and megakaryocytes and by monocyte-macrophages, respectively. These results and the characteristic morphology of the cells indicate that the culture consisted of fibroblasts only. C-myb mRNA expression was easily detected at similar levels in untreated (FIG. 3A, lane a) and sense-treated stromal cells (lane b), whereas significantly lower c-myb mRNA levels were present in cells treated with c-myb antisense oligonucleotides (lane c). Densitometric measurement of the c-myb hybridizing bands in sense versus antisense oligodeoxynucleotide-treated samples indicated that the signal from the antisense-treated samples was <10% of that from the sense-treated sample.

To determine whether inhibition of c-myb expression affected stromal fibroblast cell functions, GM-CSF, SCF, IL-6 and IL-11 mRNA levels in c-myb-sense- or antisense-treated cultures were investigated in four different experiments. High levels of GM-CSF and SCF mRNAs were detected in untreated and c-myb sense-treated cultures (FIGS. 3B and 3C lanes a and b) whereas these were reduced by >90% in cultures exposed to c-myb antisense oligodeoxynucleotides (lanes c). In contrast, IL-6 and IL-11 mRNA levels were not affected by the treatment with c-myb antisense oligodeoxynucleotides. IL-3 mRNA levels, barely detectable in stromal cells, were not modified in cultures treated with c-myb antisense oligodeoxynucleotides. Levels of β-actin mRNA, used as control, were constant.

Expression of GM-CSF and SCF in T98G Cells Constitutively Expressing c-myb

Figure 5B:
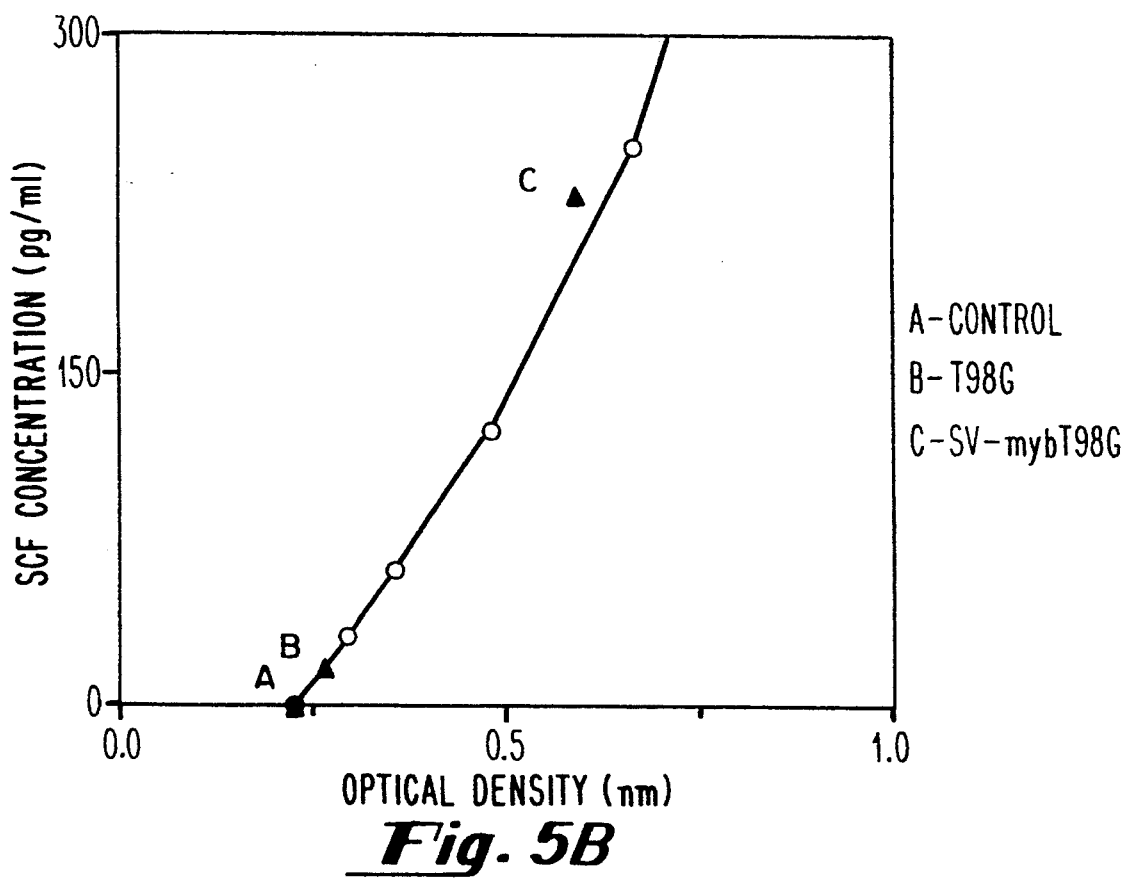
FIG. 5B shows SCF in cell-free supernatants from cultures of control and SV-myb-transfected T98G cells. Levels of SCF were measured by ELISA in RPMI-10% FBS medium (A), and in the cell-free supernatants from control T98G cells (B) and SV-myb T98G cells (C). Each point represents data collected from two independent experiments. —O— SCF standard in pg/ml; —▲— SCF detected in supernatant, in pg/ml.
Figure 5A:
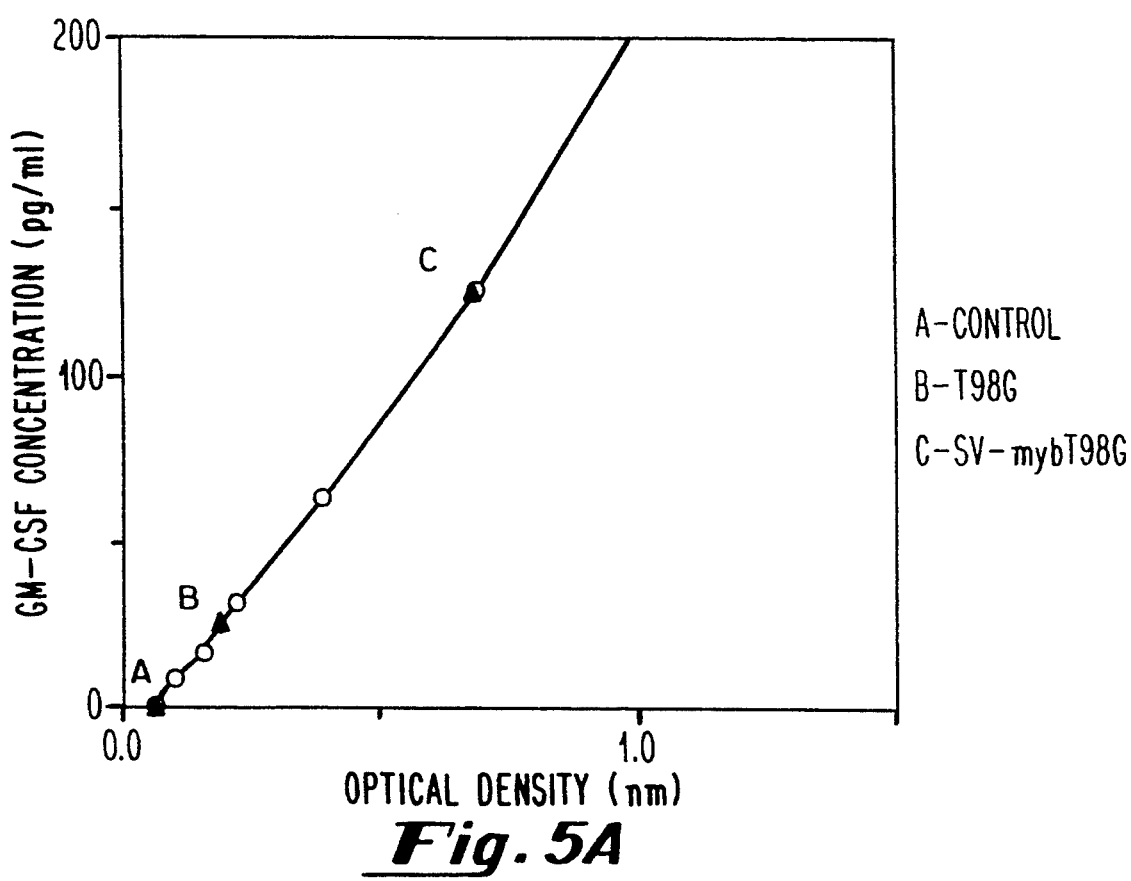
FIG. 5A shows detection of GM-CSF in cell-free supernatants from cultures of control and SV-myb-transfected T98G cells. Levels of GM-CSF were measured by ELISA in RPMI-10% FBS medium (A), and in the cell-free supernatants from control T98G cells (B) and SV-myb T98G cells (C). Each point represents data collected from two independent experiments. —O— GM-CSF standard in pg/ml; —▲— GM-CSF detected in supernatant, in pg/ml.
Figure 6A:
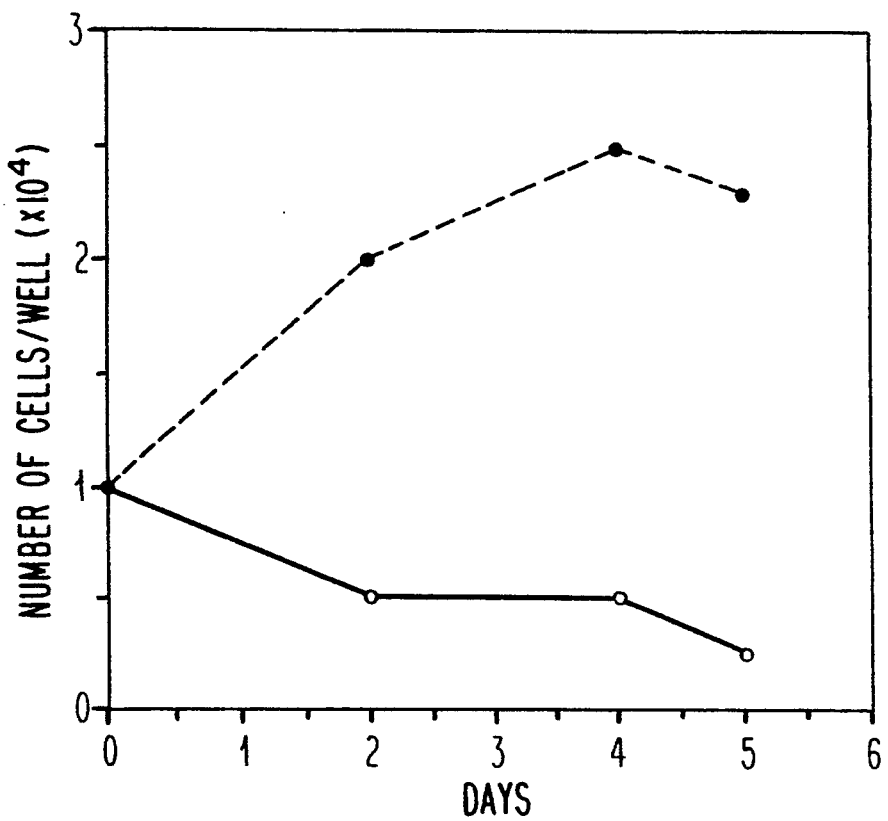
FIG. 6A show proliferation of MO7 cells upon co-culture with c-myb-transfected T98G cells. MO7 cells ($10^4$) were added to 80% confluent monolayers of adherent T98G cells transfected with pLHL4 (hygromycin resistance gene) (—0—) or co-transfected with pLHL4 and pMbml (c-myb driven by the SV-40 promoter) (- - -●- - -). The number of cells growing in suspension was counted at the indicated times.
Figure 6B:
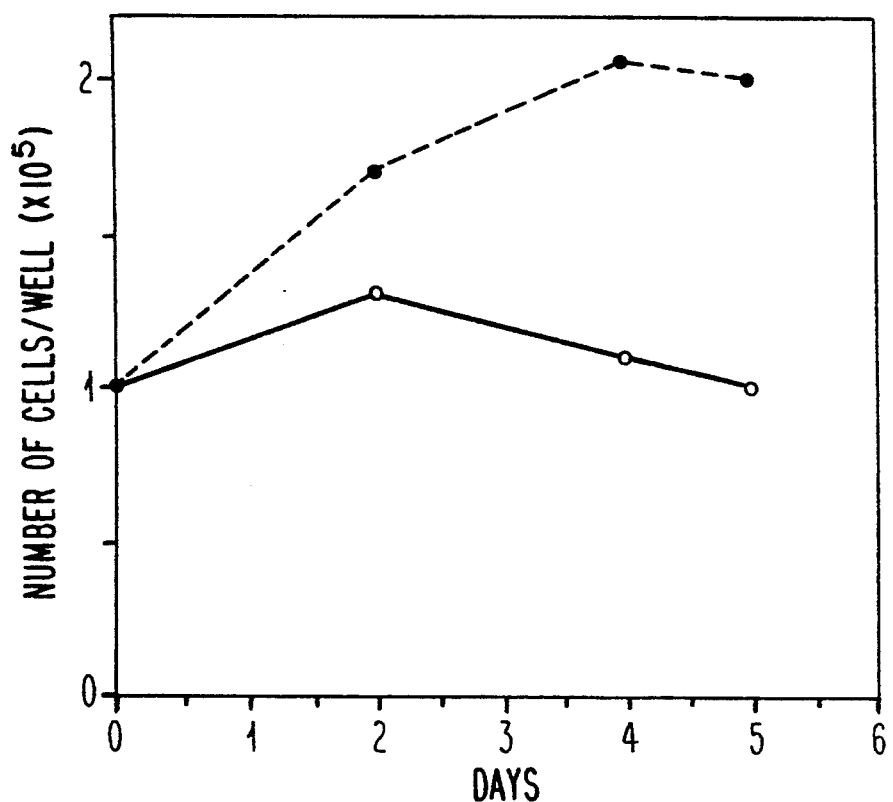
FIGS. 6B shows proliferation of MO7 cells upon co-culture with c-myb-transfected T98G cells. MO7 cells ($10^5$) were added to 80% confluent monolayers of adherent T98G cells transfected with pLHL4 (hygromycin resistance gene) (—0—) or co-transfected with pLHL4 and pMbml (c-myb driven by the SV-40 promoter) (- - -●- - -). The number of cells growing in suspension was counted at the indicated times.

To further investigate whether c-myb expression is linked to that of GM-CSF and SCF, T98G glioblastoma cells, which express undetectable or low levels of endogenous c-myb, were transfected with a human c-myb cDNA driven by the SV40 promoter in the presence of the plasmid carrying the gene encoding hygromycin resistance. After selection, a mixed cell population of T98G cells transfected with a human c-myb cDNA driven by the early SV40 promoter (SV-myb T98G) (FIG. 4A, 4B, and 4C, lanes b) and expressing the exogenous c-myb at high levels appeared to express higher levels of GM-CSF or SCF mRNA compared to T98G cells transfected only with the plasmid pLHL4 encoding hygromycin resistance (FIGS. 4A, 4B, and 4C, lanes a). In SV-myb T98G cells the level of expression of GM-CSF and SCF mRNA increased linearly with increase in the number of RCR cycles from 30 to 50. SCF mRNA was not detected in control T98G cells, whereas GM-CSF mRNA could be detected only after as many as 50 cycles of PCR amplification. In SV-myb T98G cells, SCF mRNA levels appeared essentially identical to those found in HTB9 cells, whereas GM-CSF mRNA levels were less abundant than in PHA-stimulated PBMC. GM-CSF and SCF levels were measured in the cell-free culture supernatant from the control and the SV-myb transfected T98G cells. A 3-to-4-fold and a 10-to-14-fold increase in secreted GM-CSF and SCF proteins, (FIGS. 5A and 5B,) respectively was detected in SV-myb T98G cells, compared to T98G cells transfected only with plasmid pLHL4. Biological activity of the secreted cytokines was analyzed using the acute myelogenous leukemia MO7 cell line whose proliferation is dependent on exogenously added IL-3, GM-CSF, or SCF(26–28). Either $10^4$ of $10^5$ MO7 cells were seeded on a feeder layer of exponentially growing control or SV-myb-transfected T98G cells, and the number of cells in suspension was counted at different days. MO7 cells seeded on the feeder layer of SV-myb T98G cells continued to proliferate over a five-day period. In contrast, T98G cells transfected only with plasmid pLH4 encoding hygromycin resistance were not able to support the growth of MO7 cells (FIGS. 6A and 6B). T98G cells are growth-arrested when they reach confluence; to exclude the possible presence of contaminating T98G cells among MO7 growing cells, expression of CD45, present on MO7 cells and absent on SV-myb T98G cells was analyzed by flow cytometry in the cells growing in suspension. More than 90% of the cells were CD45+, thus confirming the proliferation of MO7 cells on the feeder layer of SV-myb T98G cells.

Figure 7A:
FIG. 7A is an autoradiogram showing CAT activity in lysate of Tk-ts 13 hamster fibroblasts transfected with: lane 1) GM-CSF CAT2 only and lane 2) GM-CSF CAT 2 and pMb ml (human c-myb cDNA driven by the SV 40 promoter).
Figure 7B:
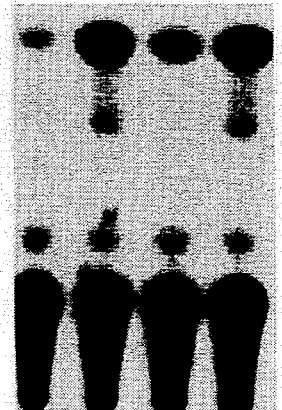
FIG. 7B is an autoradiogram showing CAT activity in lysate of: lane 1) Tk-ts13 hamster fibroblasts transfected with GM-CSF CAT 2; lane 2) SV-myb Tk-ts13 hamster fibroblasts transfected with GM-CSF CAT 2; lane 3) SV-myb Tk-ts13 hamster fibroblasts transfected with GM-CSF CAT 2 plus a 22-base synthetic oligomer containing 2Myb binding sites; lane 4) SV-myb Tk-ts13 hamster fibroblasts transfected with GM-CSF CAT 2 plus a 22-base synthetic oligomer containing mutated (3 nucleotide substitutions) Myb binding sites.

C-myb Transactivation of CAT Gene Expression Driven by the Human GM-CSF 5′ Flanking Region Containing Putative Myb Binding Sites To assess the ability of c-myb to transactivate GM-CSF, transient expression assays were performed using a CAT reporter construct containing a 600-bp fragment of the human GM-CSF 5′ flanking region found to contain several putative Myb binding sites. In Tk-ts13 hamster cells transfected at a 5:1 effector-to-reporter ratio and assayed 48 hours later, the SV40 c-myb effector plasmid induced a 5-fold increase in CAT expression driven by the 600-bp GM-CSF 5′ flanking sequence was found in SV-myb-TK-ts13 cells constitutively expressing a human c-myb cDNA (FIG. 7B, lane 2).

These latter cells were also transfected with the GM-CSFCAT2 construct in the presence of an excess (100:1, molar ratio) of a 22-base synthetic oligomer containing two canonical Myb binding sites or a 22-base synthetic oligomer with mutations at both sites. Transactivation of the GM-GSF CAT2 construct in the transfected cells was abolished by the wild type 22-mer competitor, but was unaffected by the mutated competitor (FIG. 7B, lanes 3 and 4), suggesting that the transactivation of the GM-CSF promoter directly depended on c-myb expression and interaction with Myb binding sites.

Figure 7C:
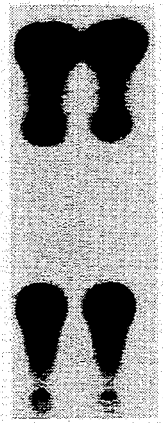
FIG. 7C is an autoradiogram showing CAT activity in lysate of: lane 1) Tk-ts13 hamster fibroblasts transfected with pSV-CAT (5 mg); lane 2) Tk-ts13 hamster fibroblasts transfected with pSV-CAT plus a 22-base synthetic oligomer containing 2 Myb binding sites.
Figure 7D:
FIG. 7D is a scintillation counting of acetylated [$^{14}$C] chloramphenicol related to CAT activity in lysate of Tk-ts 13 hamster fibroblasts transfected with: peak 1) GM-CSF CAT2 only and peak 2) GM-CSF CAT 2 and pMb ml (human c-myb cDNA driven by the SV 40 promoter).
Figure 7E:
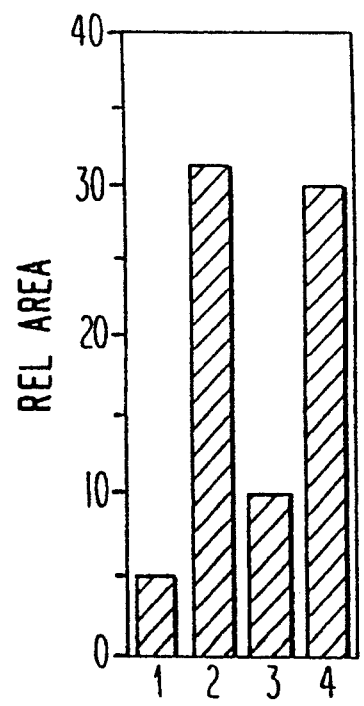
FIG. 7E is a scintillation counting of acetylated [$^{14}$C] chloramphenicol related to CAT activity in lysate of: peak 1) Tk-ts13 hamster fibroblasts transfected with GM-CSF CAT 2; peak 2) SV-myb Tk-ts13 hamster fibroblasts transfected with GM-CSF CAT 2; peak 3) SV-myb Tk-ts13 hamster fibroblasts transfected with GM-CSF CAT 2 plus a 22-base synthetic oligomer containing 2 Myb binding sites; peak 4) SV-myb Tk-ts13 hamster fibroblasts transfected with GM-CSF CAT 2 plus a 22-base synthetic oligomer containing mutated (3 nucleotide substitutions) Myb binding sites.
Figure 7F:
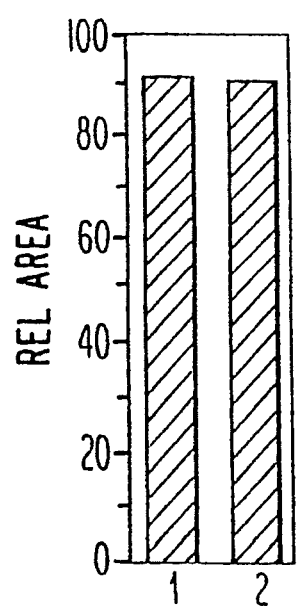
FIG. 7F is a scintillation counting of acetylated [$^{14}$C] chloramphenicol related to CAT activity in lysate of: peak 1) Tk-ts13 hamster fibroblasts transfected with pSV-CAT (5 mg); peak 2) Tk-ts13 hamster fibroblasts transfected with pSV-CAT plus a 22-base synthetic oligomer containing 2 Myb binding sites.

To demonstrate that the 22-base oligomer containing two canonical Myb binding sites was non-toxic, CAT activity was analyzed in TK-ts13 cells transfected with pSV-CAT in the presence (FIG. 7C, lane 2) or in the absence (FIG. 7C, lane 1) of excess amount (100:1, molar ratio) of the synthetic oligomer. Levels of CAT activity were identical, confirming the specificity of the effects observed.

The invention is further illustrated by the following non-limiting examples.

EXAMPLE 1

Cells and Cell Cultures

Bone marrow aspirates were obtained from the iliac crest of healthy individuals after informed consent. The cell suspensions were diluted 1:4 with Iscove's modified Dulbecco medium (IMDM), layered on Ficoll/Histopaque density gradient, and centrifuged for 30 minutes at 1,500 rpm. Light-density mononuclear cells were washed in the same medium, and plated ($5 \times 10^5$ cells/dish) into 35 mm Petri dishes (Nunc, Inc., Naperville, Ill.) in IMDM supplemented with 15% fetal bovine serum (FBS). After 90 minutes, supernatant containing non-adherent cells was discarded, and the remaining adherent cells were cultured. Culture medium was changed every three days. After 14-day culture, the number of colonies was counted under light microscope after staining with 5% crystal violet for 8 minutes. Cells to be used for RNA extraction were grown as monolayers, washed twice with Hanks balanced salt solution (HBSS), passaged four times, washed with IMDM and lysed with lysing solution directly in the plates. The cell composition of this population of stromal cells was analyzed by surface phenotyping as described below. T98G human glioblastoma cells and TK-ts13 hamster fibroblasts (kind gifts of Drs. E. Mercer and R. Baserga, respectively) were maintained in culture.

EXAMPLE 2

Indirect Immunofluorescence

Cells were grown on chamber slides (Nunc Inc., Naperville, Ill.) to subconfluency. The slides were rinsed with phosphate buffered saline (PBS) and fixed with ice-cold 100% ethanol. Following a 30-minute incubation with 1% bovine serum albumin in PBS the samples were exposed to either factor VIII- (Dako, Denmark), CD14, CDw32 or type I collagen- (ICN, Costa Mesa, Calif.) monoclonal antibodies for 45 minutes at room temperature. The slides were then rinsed with PBS and exposed to rhodamine or fluoresceine conjugated monoclonal anti-mouse-lgG antibodies (Cappel, West Chester, Pa.) for 45 minutes. Non-adherent secondary antibodies were then washed off with PBS. Non-specific binding of the antibodies was excluded by performing controls with secondary antibodies only. In additional controls, microvascular endothelial cells were stained with antibodies to factor VIII.

EXAMPLE 3

Oligomers and primers

These were synthesized on a DNA synthesizer (model 308B; Applied Biosystems, Inc., Foster City, Calif.) by means of b-cyanoethyl-phosphorymidite chemistry. The sequences of c-myb sense and antisense oligodeoxynucleotides used were 5'-GCC CGA ACA CCC CGG CAC-3' (SEQ ID NO: 1) and 5'-GTG CCG GGG TCT TGG GGC-3' (SEQ ID NO: 2), respectively. C-myb mRNA was detected by RT-PCR amplification of a segment of c-myb mRNA in the 3' untranslated region with a 5' synthetic primer 5'-ATT AGG TAA TGA ATT GTA GCC AG-3' (SEQ ID NO: 3) and a 3' synthetic primer 5'-ACT TAG AGT AAT GCT TTT ACT GA-3' (SEQ ID NO: 4). The amplification product was detected by hybridization to the synthetic oligomer included in the amplified fragment 5'-ATT TTT TTA AAA AAA AAC ATA AAA TGA TTT ATC TGG TAT TTT AAA GGA TCC-3' (SEQ ID NO: 5) encompassing nucleotides 2351-2400 of the human c-myb cDNA (Majello, B., Kenyon, L. C. and Dalla-Favera, R. (1986) Human c-myb Protooncogene: Nucleotide Sequence of cDNA and Organization of Genomic Locus, *Proc. Natl. Acad. Sci.*, U.S.A., 83:9616). βactin mRNA levels were also analyzed by RT-PCR. The 5' primer corresponds to nucleotides 224–244; the 3' primer corresponds to nucleotides 411–433 of β-actin cDNA, a 39-base probe used to detect the amplification product corresponds to nucleotides 258–296 (Tukunaga, K. et al., (1986), Nucleotide Sequence for a Full-Length cDNA for Mouse Cytoskeletal β-actin mRNA, *Nucl. Acid. Res.* 14:2829). GM-CSF mRNA was detected by RT-PCR technique with a pair of synthetic primers: 5' primer 5'-ATG TGA ATG CCA TCC AGG AG-3' (SEQ ID NO: 6), 3' primer 5'-CTT GTA GTG GCT GGC CAT CA-3' (SEQ ID NO: 7) and detected with a synthetic probe 5'-TAG AGA CAC TGC TGC TGA GA-3' (SEQ ID NO: 8). SCF mRNA was detected using the following set of primers: 5' primer 5'-ATG AAG AAG ACA CAA ACT TGG-3' (SEQ ID NO: 9), 3' primer 5'-GCT CAG AAG ATC AGT CAA GCT-3' (SEQ ID NO: 10), and detected by synthetic oligomer probe 5'-GCC GAG CTG GAC AGC ACC GTG CTC CTG ACC CGC TCT CTC-3' (SEQ ID NO: 11). IL-6 mRNA was detected using the following set of primers: 5' primer 5'-AAG ATT CAT ACC TCA GAG CG-3' (SEQ ID NO: 12), 3' primer 5'-ATG AGA TCA CCT AGT CCA CC-3' (SEQ ID NO: 13), and detected by synthetic oligomer probe 5'-AGC CCA GAC TCG AAT TCT GGT TCT GCC AAA-3' (SEQ ID NO: 14). IL-11 mRNA was detected using the following set of primers: 5' primer 5'-ATG AAC TGT GTT TGC CGC-3' (SEQ ID NO: 15), 3' primer 5'-CCC CTG AGC TGG GAA TTT-3' (SEQ ID NO: 16), and detected by synthetic oligomer probe 5'-GCC GAG CTG GAC AGC ACC GTG CTC CTG ACC CGC TCT CTC-3' (SEQ ID NO: 17).

EXAMPLE 4

Oligomer Treatment of the Cells

Normal bone marrow (NBM) cells were plated into 35 mm dishes (Nunc, Inc., Naperville, Ill.) in 1 ml IMDM 1640 supplemented with 15% FBS. C-myb sense and antisense oligodeoxynucleotides were added three times during a 14-day culture: 40 to 120 µg/ml as indicated, were added during the first 18-24 hours of incubation (37° C., 5% $CO_2$), half of the initial dose was added on Day 3, and a third dose (50% of initial dose) was added on Day 6 after changing the medium. On Day 14, the medium was discarded, the cells were stained with 5% crystal violet for 8 minutes, and the number of colonies per plate and cell number per colony were determined.

EXAMPLE 5

Transfection

T98G human glioblastoma cells were transfected using the calcium-phosphate precipitation method which is well known in the art. Briefly, $2 \times 10^5$ cells were either cotransfected with 10 µg of the plasmid pMbm1 which contains the human c-myb cDNA under control of the SV40 early promoter and enhancer, and 1 pg of the plasmid pLHL4 which contains the gene encoding hygromycin resistance or transfected with the plasmid pLHL4 only. After 12-day selection in culture medium containing 0.5 mg/ml of hygromycin B (Calbiochem, San Diego, Calif.), colonies were pooled and cultured in medium containing 0.3 mg/ml of hygromycin B.

EXAMPLE 6

Detection of c-myb, βActin, GM-CSF and SCF mRNA Transcripts in Marrow Fibroblasts and in T98G To analyze the effect of c-myb sense and antisense oligodeoxynucleotide treatment on c-myb expression, $10^5$ marrow fibroblasts obtained after the fourth passage were plated into 35 mm plastic dishes (Nunc, Inc., Naperville, Ill.), and were left untreated or exposed to c-myb sense or antisense oligodeoxynucleotides (40 µg/ml at time 0; 20 µg/ml at 24 hours); 24 hours later, cells were collected separately from each experimental group before extracting total RNA in accordance with standard methods. RNA from each group was divided into four identical portions, and reverse transcribed using 400 U of Moloney murine leukemia virus reverse transcriptase (Bethesda Research Laboratories, Gaithersburg, Md.), and 0.1 µg of 3' primers of c-myb, β-actin, GM-CSF and SCF for 1 hour at 37° C. Resulting cDNA fragments were amplified with 5 U of Taq polymerase (Perkin-Elmer-Cetus, Norwalk, Conn.) in the presence of 3' and 5' primers generating c-myb, β-actin, GM-CSF and SCF fragments during 50 cycles of PCR. Amplified DNA was electrophoresed, transferred to Zetabind nylon filters (Cuno, Inc., Meriden, Conn.) and detected by Southern hybridization with [$^{32}$P]ATP end-labeled c-myb, β-actin, GM-CSF or SCF synthetic probes. Densitometric analysis of hybridization bands were performed using an Ultro Scan XL (Pharmacia LKB) apparatus.

GM-CSF and SCF mRNA levels were determined in 1 µg of total RNA derived from parental and SVmyb-transfected T98G cells. As positive control for the expression of GM-CSF and SCF, RNA derived from phytohemagglutinin (PHA)-stimulated blood mononuclear cells (PBMC) and the bladder carcinoma HTB9 line, respectively, was used. RNA from each sample was divided into four portions, and c-myb, GM-CSF, SCF and β-actin expression was determined by RT-PCR technique. As negative control, RT-PCT amplifications were performed in the absence of RNA.

EXAMPLE 7

Detection of GM-CSF and SCF in Cell-Free Culture Supernatants of SV-myb-Transfected T98G Cells Cell-free culture supernatants were collected from exponentially growing T98G transfected with plasmid pLHL4 encoding hygromycin resistance and SV-myb-transfected T98G cells cultured in the presence of 10% FBS. Supernatants were sterilized by filtration through

EXAMPLE 8

Isolation of the 5' Flanking Region of Human GM-CSF Gene and Plasmid Construction A 600 bp fragment of the 5' flanking region of the human GM-CSF gene was isolated by PCR amplification of placenta genomic DNA using the following primers: 5' primer 5'-AAG CTT GCT GAG AGT GGC TGC-3' (SEQ ID NO: 18); 3' primer 5'-CAG AGA ACT TTA GCC TTT CTC-3' (SEQ ID NO: 19). The amplified fragment was then subcloned into the SmaI site of the Bluescript sector (Strategene), 5' of the T7 promoter and subjected to sequence analysis to confirm its identity with the 5' flanking segment of the human GM-CSF gene. This plasmid was called GMCSF17. A CAT construct was prepared after digestion of GMCSF17 with EcoRV and HindIII to isolate the 600 bp fragment and cloning it into pucCAT linearized using HindIII and SalI restriction enzymes in order to obtain the GMCSF fragment in sense orientation with respect to the CAT gene. This construct was named GM-CSF CAT2.

EXAMPLE 9

Transient CAT Analysis

CAT assays were performed in accordance with methods well known in the art. Briefly, 2 μg of CAT reporter plasmid was transfected with or without 8 μg of effector plasmid plus 1 μg of pSV-β-gal which contains the bacterial β-galactosidase gene driven by the SV40 promoter as an internal control of transfection efficiency, into wild-type or SV-myb-transfected TK-ts13 Syrian hamster fibroblasts using the well known calcium-phosphate precipitation method. Forty-eight hours after transfection, cells were harvested and proteins were extracted by freeze/thawing and normalized for transfection efficiency by β-galactosidase assay as described by the manufacturer (Promega). For each assay, cellular lysates were incubated with [$^{14}$C]-chloramphenicol and acetyl-CoA for one hour at 37° C. Transactivation of reporter constructs was assayed measuring the amount of acetylated [$^{14}$C]-chloramphenicol by thin-layer chromatography followed by autoradiography and scintillation counting.

---

What is claimed:

1. A cell line of c-myb-transfected T98G human glioblastoma cells capable of producing granulocyte/macrophage colony stimulation factor or stem cell factor.

2. A cell line of claim 1 having cells co-transfected with a first plasmid containing human c-myb cDNA and a second plasmid containing the gene encoding hygromycin resistance.

3. A cell line of claim 2 wherein said second co-transfected plasmid is the plasmid pLHL4.

4. A cell line of claim 2 wherein said first plasmid comprises a full-length c-myb cDNA under the control of the SV40 promoter.

5. A cell line of claim 4 wherein said first co-transfected plasmid is the plasmid pMbm1.

6. A method of producing granulocyte/macrophage-colony stimulation factor or stem cell factor comprising:

culturing T98G human glioblastoma cells;

co-transfecting said cultured T98G human glioblastoma cells with a first plasmid containing human c-myb cDNA and a second plasmid containing the gene encoding hygromycin resistance;

selecting for hygromycin-resistant cells in culture medium containing hygromycin B;

culturing the cells so selected in medium containing hygromycin B;

recovering granulocyte/macrophage-colony stimulation factor or stem cell factor from the culture medium.

7. The method of claim 6 wherein said second co-transfected plasmid is the plasmid pLHL4.

8. The method of claim 6 wherein said first co-transfected plasmid comprises a full-length c-myb cDNA under the control of the SV40 promoter.

9. The method of claim 8 wherein first co-transfected plasmid is the plasmid pMbm1.

* * * * *